United States Patent
Chen

(10) Patent No.: US 9,328,200 B2
(45) Date of Patent: May 3, 2016

(54) BRANCHED POLYMERIC QUATERNARY AMMONIUM COMPOUNDS AND THEIR USES

(71) Applicant: Hwang-Hsing Chen, Fort Worth, TX (US)

(72) Inventor: Hwang-Hsing Chen, Fort Worth, TX (US)

(73) Assignee: ULTRASCI DISCOVERY LLP, Allen, TX (US)

( * ) Notice: Subject to any disclaimer, the term of this patent is extended or adjusted under 35 U.S.C. 154(b) by 0 days.

(21) Appl. No.: 14/326,467

(22) Filed: Jul. 9, 2014

(65) Prior Publication Data

US 2016/0009861 A1    Jan. 14, 2016

(51) Int. Cl.

| | |
|---|---|
| *C08G 73/02* | (2006.01) |
| *A01N 43/90* | (2006.01) |
| *A01N 33/12* | (2006.01) |
| *C08G 73/06* | (2006.01) |
| *A61K 47/34* | (2006.01) |
| *A61K 9/00* | (2006.01) |
| *A61L 12/14* | (2006.01) |
| *C11D 3/00* | (2006.01) |

(52) U.S. Cl.
CPC ............... *C08G 73/02* (2013.01); *A01N 33/12* (2013.01); *A01N 43/90* (2013.01); *A61K 9/0048* (2013.01); *A61K 47/34* (2013.01); *A61L 12/145* (2013.01); *C08G 73/0694* (2013.01); *C11D 3/0078* (2013.01)

(58) Field of Classification Search
CPC .............................. C08G 73/02; A01N 33/02
See application file for complete search history.

(56) References Cited

U.S. PATENT DOCUMENTS

| | | | | |
|---|---|---|---|---|
| 7,655,662 B2 * | 2/2010 | Hellberg | ............... | A61K 9/0048 514/218 |
| 8,431,751 B1 * | 4/2013 | Castillo | ................... | C08G 73/02 528/397 |

* cited by examiner

*Primary Examiner* — Gina Justice

(57) ABSTRACT

Biocidal branched quaternary ammonium polymers are made by condensing a difunctional halide with a trifunctional tertiary amine and optionally with a difunctional amine. The branched quaternary ammonium polymers have 2-dimensional conformation that provides better coverage over the surfaces of microorganisms and enhances efficacy as biocides as compared to most commercially available linear (one-dimensional) quaternary ammonium polymers. The bulkier 2-dimensional conformation of this invention limits the uptake, accumulation and release of these branched polymers to and from contact lenses. Therefore, these branched quaternary ammonium polymers can reduce the cytotoxicity, enhance compatibility and suitable for ophthalmic use. The highly branched polymers can be prepared with minimum or no difunctional tertiary amines. The lightly branched polymers can be prepared with of a minimum ratio of trifunctional tertiary amines/difunctional tertiary amines.

19 Claims, No Drawings

BRANCHED POLYMERIC QUATERNARY AMMONIUM COMPOUNDS AND THEIR USES

CROSS-REFERENCE TO RELATED APPLICATION

The present application claims priority from U.S. Provisional Application Ser. No. 61/957,967, filed Jul. 17, 2013.

FIELD OF INVENTION

The present invention relates to biocidal branched polymers comprising quaternary ammonium salts. The quaternary ammonium salts are made by condensing a difunctional halide with a trifunctional amine and optionally with a difunctional amine to control the number of branches. The quaternary ammonium salts can also be made by condensing a difunctional amine with a trifunctional chloride and optionally with a difunctional chloride to control the number of branches. The preferred trifunctional tertiary amines include 2-[(dimethylamino)-methyl]tetramethyl-1,3-propanediamine, hexamethyl-1,2,3-propanetriamine, N-methyl-N,N-bis[3-(dimethylamino)-propyl]amine and pentamethyldiethylenetriamine. The preferred trifunctional chlorides include tris(chloromethyl)benzene and tris(chloromethyl)pyridine. The preferred difunctional tertiary amines include 1,4-diazobicyclo[2,2,2]octane, 1,4-dimethylpiperazine, tetramethylethylenediamine, tetramethylpropylenediamine, and 1,3-bis(dimethylamino)-2-hydroxypropane. The preferred difunctional halides include 1,3-dichloro-2-propanaol, 1,3-dibromo-2-propanol, bis(chloroethyl)ether, 1.4-dichloro-2-butene, bis(chloromethyl)benzene and bis(chloromethyl)pyridine. The branched polymers exhibit higher biocidal efficacy especially against algae and fungi presumably because of the better surface coverage of the microorganisms. The branched polymers have 2-dimensional network and can improve compatibility with sensitive tissues and are highly safe for the eyes, and have a negligible adsorption onto contact lenses and suitable for ophthalmic use.

BACKGROUND ART

A biocide is a chemical substance, which can deter, render harmless, or exert a controlling effect on any harmful organism. Biocides are commonly used in medicine, agriculture, forestry, and industry.

The development of new and useful biocides requires consideration of many elements such as the following: the type of organism whose control is desired; the manner in which the biocide is to be deployed; the costs of preparing and delivering the biocide; environmental or disposal issues; and so on. Depending on the potential use envisioned, primary considerations are likely to include both its potency against the organisms targeted, as well as its biocompatibility, e.g. lack of toxicity against the humans or animals which may come into contact with it. Biocides may have a broad or narrow spectrum of activity.

Many of the current organic biocides have two functional group components, a hydrophilic/polar part and a hydrophobic/oil part. Broad-spectrum biocides may require higher hydrophobic elements in order to penetrate biological membranes and achieve their full potency. Hydrophobicity in biocides can be achieved through incorporation of long chain hydrocarbons or aryl groups into the structure of the molecule. However, the current organic biocides used in the pharmaceutical field are focused on improving biocompatibility to reduce the toxicity against human tissues. Discovery of biocides with a desired balance between hydrophilicity and hydrophobicity for its field of use is important and highly challenging.

Benzalkonium cholide (BAC, BAK) is one of the most common and potent biocide being used in the ophthalmic solution. Although necessary for efficacy, the hydrophobic benzyl and long chain hydrocarbons can also cause damage to ocular tissues. The small molecule of BAC also facilitates penetration and accumulation readily into contact lens and causes irritation when worn in the eye.

For their potential in overcoming some of the disadvantage of the smaller organic monomeric compound described above, polymeric quaternary ammonium compounds has been investigated for a number of years.

For example, British Patent No. 536,017 (Aug. 30, 1941), assigned to E. I. DuPont de Nemours (the "DuPont Patent"), discloses linear polymeric quaternary ammonium compounds and methods for their preparation. The compounds of the DuPont Patent were envisioned to be useful in photographic processing, to treat leather, as mold inhibitors and pesticides, and as modifying agents. There is, however, no mention of use of these compounds as disinfectants or preservatives in pharmaceutical products.

U.S. Pat. No. 3,931,319 (Jan. 6, 1976), U.S. Pat. No. 4,001,432 (Jan. 4, 1977) and U.S. Pat. No. 4,012,446 (Mar. 15, 1977), all issued to Green, et al., disclose a group of high molecular weight "capped" linear polymeric quaternary ammonium compounds found to be effective microbiocides (antimicrobials). In a continuation-in-part application, now U.S. Pat. No. 4,027,020 (May 31, 1977), Green, et al. disclose a process for making randomly capped linear polymeric quaternary ammonium compounds; that is, the polymers produced by the improved process include those with very short chain lengths as well as those having relatively long chain lengths. These compounds were also found to have antimicrobial activity.

U.S. Pat. No. 4,407,791 (Oct. 4, 1983) and U.S. Pat. No. 4,525,346 (Jun. 25, 1985), both issued to Stark, disclose disinfecting solutions for contact lenses, wherein the aqueous solutions contain the Green, et al. polymers, including the compound polyquaternium-1, commercially known as Onamer M® or PolyQuad®.

U.S. Pat. No. 4,110,263 (Lindemann et al.) describes mild cleansing compositions containing alkyleneoxylated bisquaternary ammonium compounds.

U.S. Pat. No. 4,581,058 (Apr. 8, 1986) describes polyalkyleneurea containing quaternary ammonium antimicrobial agents.

U.S. Pat. No. 5,380,303 (Jan. 10, 1995) describes polyoxyalkylene containing quaternary ammonium antimicrobial agents.

U.S. Pat. No. 6,528,048 (Mar. 4, 2003) describes polyhydroxyalkylene containing quaternary ammonium antimicrobial agents.

U.S. Pat. No. 8,093,352 (Jan. 10, 2012) describes polyalkylene oxide containing quaternary ammonium antimicrobial agents.

U.S. Pat. No. 8,309,679 (Nov. 13, 2012), U.S. Pat. No. 8,106,151 (2012), U.S. Pat. No. 7,999,064 (2011), and U.S. Pat. No. 7,705,112 (2010) describe novel methods of making quaternary ammonium antimicrobial agents with improved efficacy and minimum cytotoxicity.

U.S. Pat. No. 8,431,751 (Apr. 30, 2013) describes polymeric quaternary ammonium compounds with vicinal hydroxyl groups as antimicrobial agents.

However, the PolyQuad® has limited antimicrobial efficacy, especially against fungi and mold, while polyhexamethylene biguanide is known to be irritating to ocular tissues. All of the prior art are related to linear polymeric quaternary ammonium compounds and none of branched polymeric quaternary ammonium compounds are disclosed. There still exists a need for biocides with suitable combination of the following: an effective balance of hydrophobic and hydrophilic elements; useful antimicrobial activity; non-irritating; low toxicity; compatibility with the materials and tissue with which they come into contact.

SUMMARY OF THE INVENTION

The present invention is directed to branched polymeric quaternary ammonium compounds. In particular, this invention relates to new polymeric quaternary ammonium compounds, which contain branched quaternary ammonium groups with 2-dimensional networks for the maximal surface coverage of the microorganisms to enhance antimicrobial efficacy and for minimal uptake, accumulation and release of contact lenses to enhance ocular safety. The present invention also relates to the use of these compounds as biocide in the industry, especially in pharmaceutical and lens care products. In particular, the present invention relates to the use of these new compounds as preservatives for ophthalmic, otic or nasal compositions and as disinfectants for contact lens care products.

The compounds of the present invention differ from prior compounds through the introduction of branched quaternary ammonium groups. Without wishing to be bound by theory, it is thought that the branched quaternary ammonium groups may increase antimicrobial efficacy by maximal surface coverage with the two dimensional conformation and enhance ocular comfort by minimum uptake and release on contact lenses. Other features and advantages of the invention will become apparent from the following detailed description and claims.

DESCRIPTION OF THE INVENTION

The novel biocides of this invention comprise a polymer having at least one of branched quaternary ammonium units of the following formula:

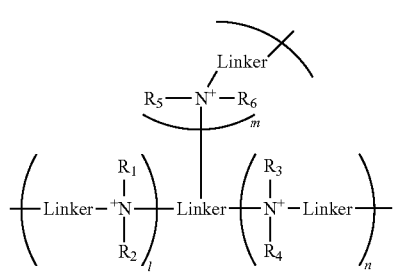

Formula 1

Wherein R1, R2, R3, R4, R5, and R6 represent alkyl groups have 1-3 carbon atoms optionally substituted with OH, OR1, aryl groups or quaternary ammoniums groups;

Linkers represent independently the same or different linkage groups with 2, 3, or more points of connections for quaternary ammonium groups and at least one of the linkers has 3 or more connections or at least 0.01% of the linker has 3 or more connections;

l, m, n represent integer varying from 1 to 1000, preferably from 1 to 500.

The preferred biocides of the present invention comprise a branched polymer of the following units:

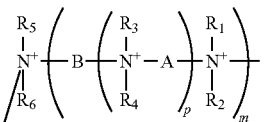

Formula 2

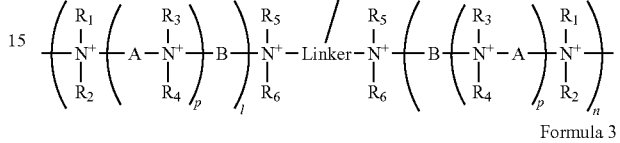

Formula 3

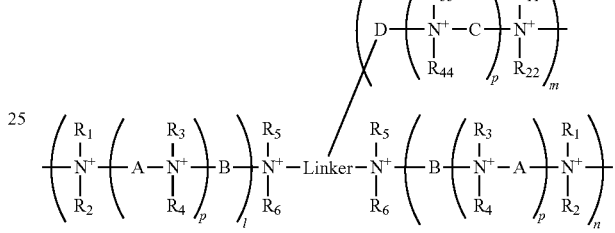

Wherein A, B, C, and D are independently selected from the group consisting of $-C_2H_4-$, $-C_3H_6-$, $-C_4H_6-$, $-CH_2-CH(OH)-CH_2-$, $-CH_2-CH(OH)-CH(OH)-CH_2-$, $-CH_2-CH_2-O-CH_2-CH_2-$, $-CH_2-(C_6H_4)-CH_2-$, $-CH_2-(C_5H_3N)-CH_2-$;

R1, R2, R3, R4, R5, R6, R11, R22, R33 and R44 independently represent alkyl groups having 1-3 carbon atoms optionally substituted with $-OH$, aryl, heteroaryl groups or quaternary ammonium;

R1 and R3 or R2 and R4 or R11 and R33 or R22 and R44 can connect together to form an ethylene or propylene linkage;

Linkers independently represent

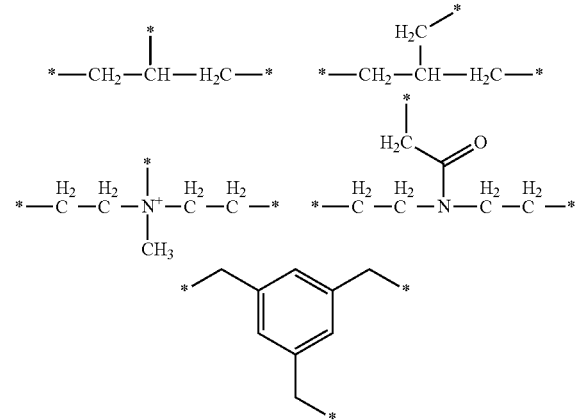

p represents integer 0 or 1;

l, m, and n represent integer varying from 1 to 1000, preferably from 1 to 500;

The counter ions include, for example, $F^-$, $Cl^-$, $Br^-$, $SO_4^{-2}$, $HSO^{4-}$, $HCO^{3-}$ and $H_2BO^{3-}$.

In the above formula, the preferred groups represented by A, B, C, and D include —$CH_2$—$CH_2$—, —$CH_2$—$CH_2$—$CH_2$—, —$CH_2$—CH=CH—$CH_2$—, —$CH_2$—CH(OH)—$CH_2$—, —$CH_2$—CH(OH)—CH(OH)—$CH_2$—, —$CH_2$—$CH_2$—O—$CH_2$—$CH_2$—, —$CH_2$—($C_6H_4$)—$CH_2$—, —$CH_2$—($C_5H_3N$)—$CH_2$—;

The groups represented by R1, R2, R3, R4, R5, R6, R11, R22, R33, and R44 are, for example, —$CH_3$, —$C_2H_5$, —$C_3H_7$, —$C_3H_6OH$, —$C_3H_6OCH_3$, —$CH_2$—($C_6H_5$), —$CH_2$—($C_5NH_4$), —$CH_2$—($C_6H_4$)—$CH_3$, and $CH_2CH_2$—N+$(CH_3)_3$.

The preferred branched units of the present invention are exampled in but not limited to the following examples;

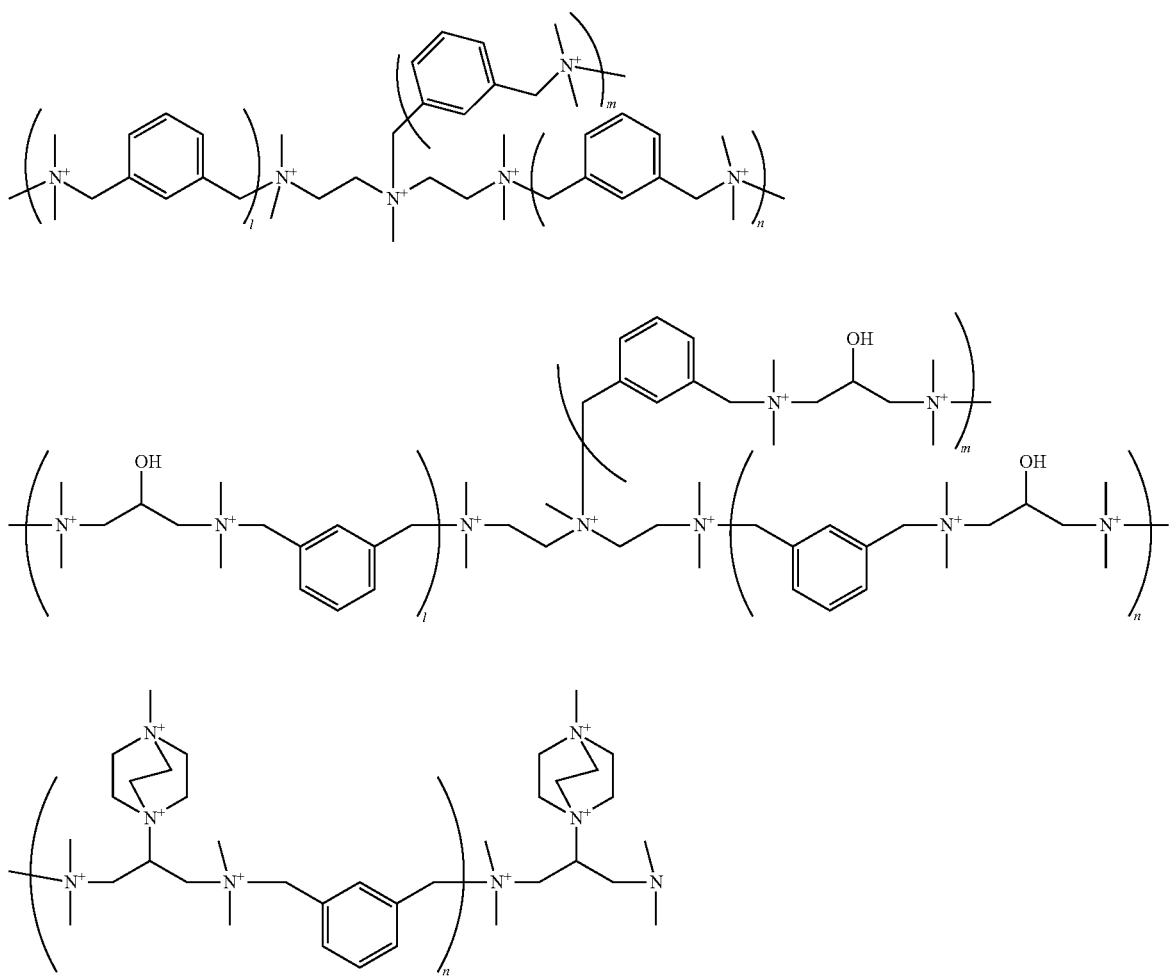

The biocides of the present invention have broad spectrum of antimicrobial activity and can be used in many applications including ophthalmic solutions. The ophthalmic solutions of the present invention can be formulated in various compositions, particularly as disinfectants in contact lens care products and as preservatives in ophthalmic, nasal or otic compositions, and are especially suitable for use in ophthalmic compositions such as artificial tears or topical ophthalmic pharmaceutical preparations. The types of compositions which may be preserved by the compounds of formula (I) include: ophthalmic pharmaceutical compositions, such as those described below; otic pharmaceutical compositions, such as topical compositions used in the treatment of bacterial infections or inflammation of the ear; dermatological compositions, such as anti-inflammatory compositions, as well as shampoos and other cosmetic compositions; and various other types of pharmaceutical compositions. In general, the polymers of the present invention will be present in the compositions at a concentration between about 0.00001 and 1.0 percent by weight/volume percent (w/v %). If used as a disinfectant, the polymers are preferably present at a concentration of between about 0.0005 and 0.5 w/v %; if used as a preservative; the polymers are present at a concentration between about 0.00005 and 0.05 w/v %. It is preferred that the polymers are present at a concentration of between 0.001 and 0.05 w/v % if used as a disinfectant and between 0.0001 and 0.01 w/v % if used as a preservative.

The compositions of the present invention may additionally contain other components, for example, buffers, tonicity adjusting agents, chelating agents, surfactants, solubilizers, active pharmaceutical agents, preservatives, pH adjusting agents and carriers.

In the case of contact lens and ophthalmic solutions, for example, various agents are added to enhance compatibility with the eye. To avoid stinging or irritation it is important that the solution possess a tonicity and pH within the physiological range, e.g., 200-350 mOsmole for tonicity and 6.5-8.5 for pH. To this end, various buffering and osmotic agents are often added. The simplest osmotic agent is sodium chloride since this is a major solute in human tears. In addition propylene glycol, lactulose, trehalose, sorbitol, mannitol or other osmotic agents may also be added to replace some or all of the sodium chloride. Also, various buffer systems such as citrate, phosphate (appropriate mixtures of $Na_2HPO_4$, $NaH_2PO_4$, and $KH_2PO_4$), borate (boric acid, sodium borate, potassium tetraborate, potassium metaborate and mixtures), bicarbonate, and tromethamine and other appropriate nitrogen-containing buffers (such as ACES, BES, BICINE, BIS-Tris, BIS-Tris Propane, HEPES, HEPPS, imidazole, MES, MOPS, PIPES, TAPS, TES, Tricine) can be used to ensure a physiologic pH between about pH 6.5 and 8.5. Borate and polyol systems may also be used to provide buffering, to enhance antimicrobial activity, or to provide both buffering and an enhancement of antimicrobial activity, or other useful properties to the compositions of the invention. The borate and polyol systems, which may be used, include those described in U.S. Pat. Nos. 6,849,253; 6,503,497; 6,365,636; 6,143,799; 5,811,466; 5,505,953; and 5,342,620; the entire contents of each are hereby incorporated into the present specification by reference.

The borates, which may be used in the compositions of the present invention, include boric acid and other pharmaceutically acceptable salts such as sodium borate (borax) and potassium borate. As used herein, the term "borate" refers to all pharmaceutically suitable forms of borates, as well as metaborates. Borates are common excipients in ophthalmic formulations due to good buffering capacity at physiological pH and well-known safety and compatibility with wide range of drugs and preservatives.

In addition to the compounds of formula (1, 2, and 3) described above, the compositions of the present invention may contain one or more additional antimicrobial agent. The invention is not limited relative to the types of additional antimicrobial agent that may be utilized. The preferred biocides include: polyhexamethylene biguanide polymers ("PHMB"), polyquatemium-1, and the amino biguanides described in U.S. Pat. No. 6,664,294, the entire contents of which are hereby incorporated in the present specification by reference.

Amidoamines, amino alcohols, and borate/polyol complexes may also be utilized to enhance the antimicrobial activity of the compositions described herein. The preferred amidoamines are myristamidopropyl dimethylamine ("MAPDA") and related compounds described in U.S. Pat. No. 5,631,005 (Dassanayake, et al.). The preferred amino alcohols are 2-amino-2-methyl-1-propanol ("AMP") and other amino alcohols described in U.S. Pat. No. 6,319,464 (Asgharian). The entire contents of the '005 and '464 patents are hereby incorporated in the present specification by reference.

The following schemes further illustrate certain embodiments of the invention. These examples are provided to aid in the understanding of the invention and are not to be construed as limitations thereof.

Scheme 1

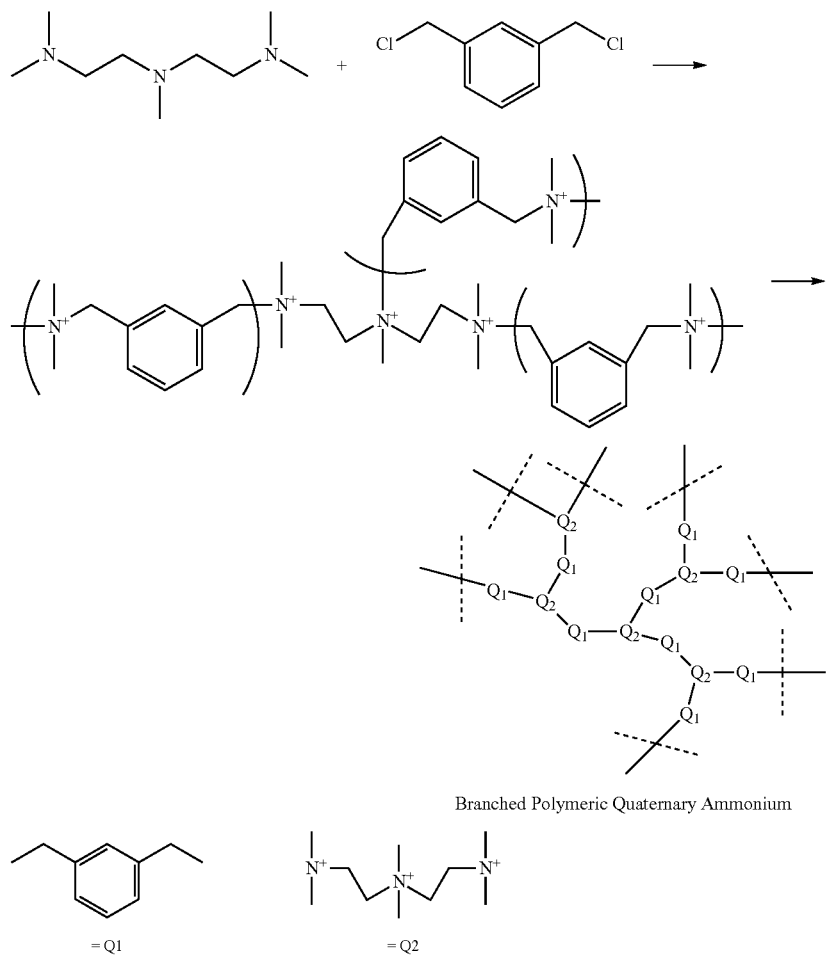

Branched Polymeric Quaternary Ammonium

Example 1

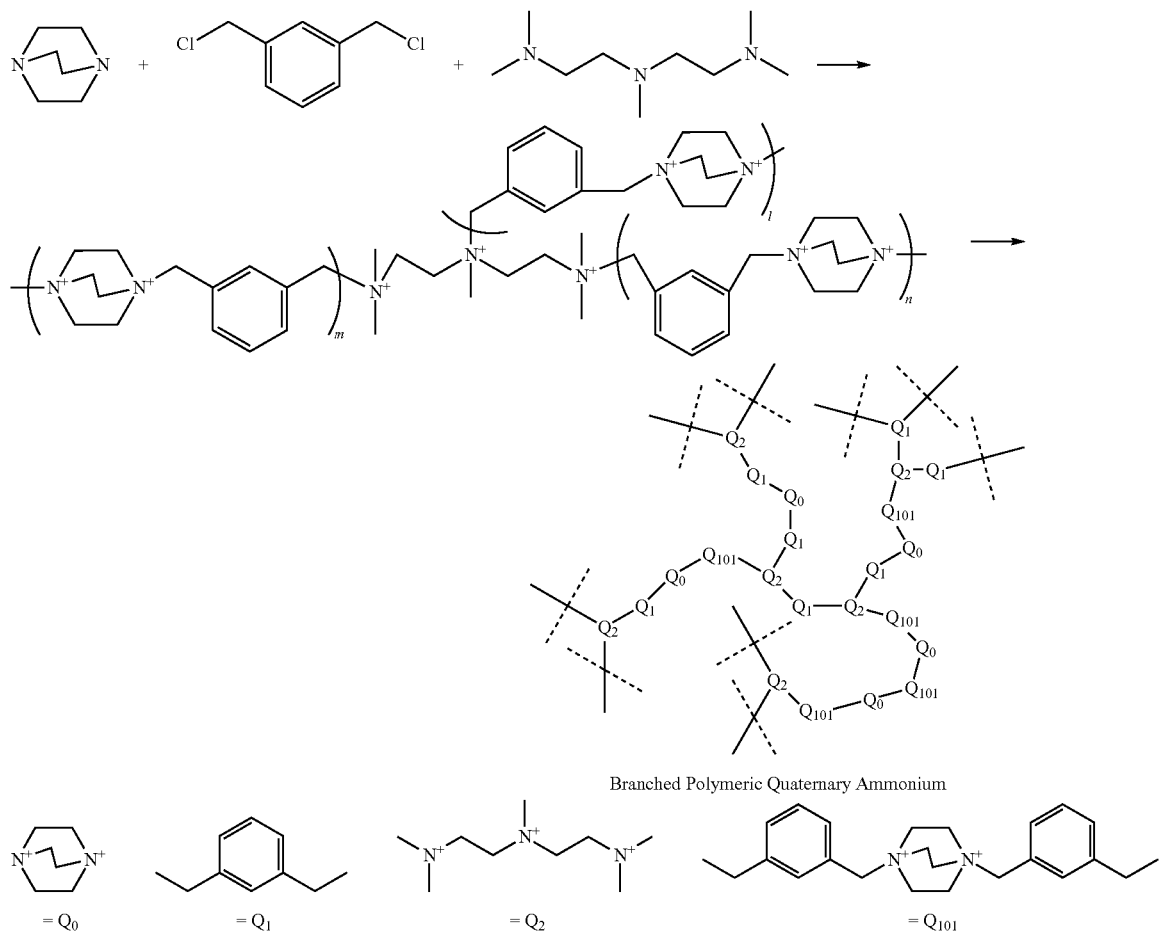

Branched Polymeric Quaternary Ammonium

Example 2

The polymer with the formula 3 was obtained by a synthetic method described below.

To a mixture of 1,4-diazobicyclo[2,2,2]octane (DABCO) (1.00 g, 8.91 mmol) in water (5 mL) was added slowly 1,3-dichloropropanol (1.26 g, 9.81 mmol), stirred for 1 hour at room temperature and then the mixture was heated at 70° C. overnight. To this mixture was added pentamethyldiethylenetriamine (0.077 g, 0.45 mmol) and 5 mL of water and the mixture was heated at 80° C. overnight. The reaction mixture was cooled at 0° C. and the polymer was precipitated by addition of acetone to give a white gel. The gel was dissolved in methanol and precipitated again with acetone. The white precipitate was dried in vacuum overnight. Nuclear magnetic resonance spectrum and other analysis methods confirmed the structure of the above polymer.

Example 2

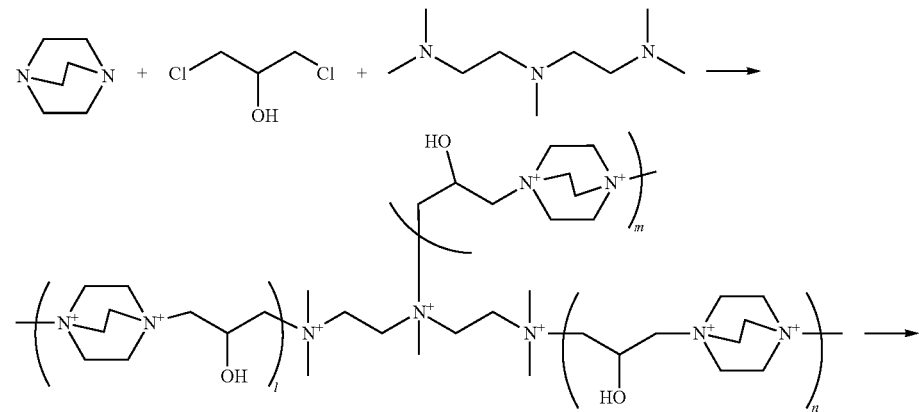

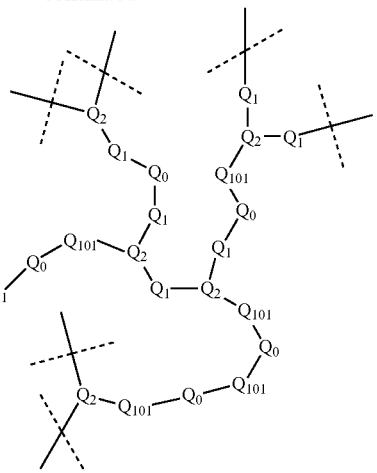
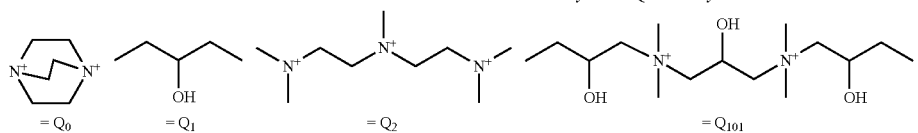
Scheme 2
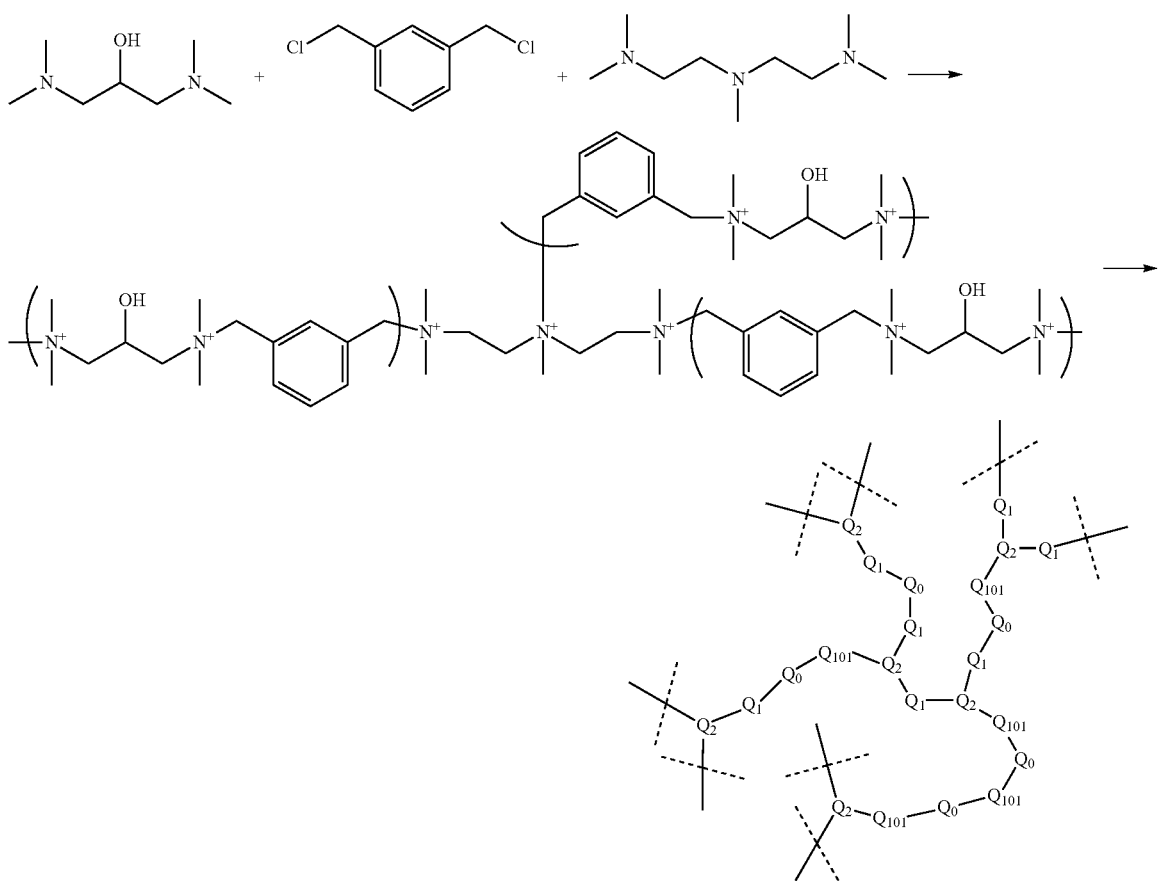
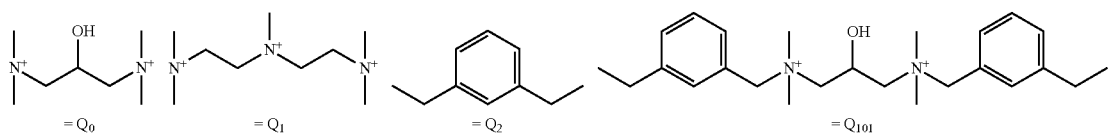

-continued
Scheme 3

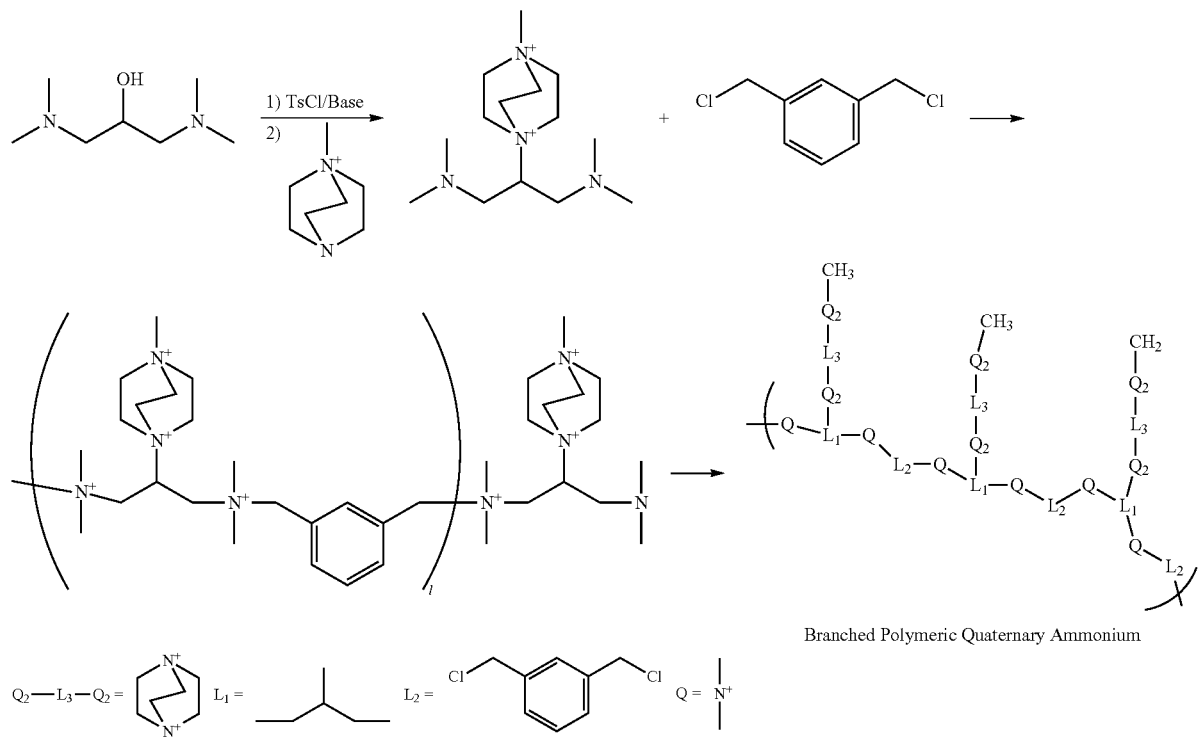

Branched Polymeric Quaternary Ammonium

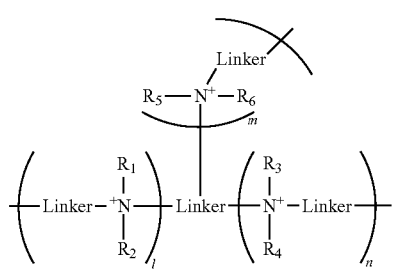

Example 1

The polymer with the formula 3 was obtained by a synthetic method described below.

To a mixture of 1,4-diazobicyclo[2,2,2]octane (DABCO) (0.50 g, 4.46 mmol), pentamethyldiethylenetriamine (0.077 g, 0.45 mmol) in methanol (25 mL) was added slowly dichloride (0.936 g, 5.35 mmol), stirred for 2 hour at room temperature and then the mixture was heated at 80° C. overnight. Methanol was evaporated to give a white solid that was dissolved in a mixture of methanol/water (20 mL/5 mL) and heated at 80° C. overnight. The reaction mixture was cooled at 0° C. and the polymer was precipitated by addition of acetone to give a white gel. The gel was dissolved in methanol and precipitated with acetone. The white precipitate was dried in vacuum overnight. Nuclear magnetic resonance spectrum and other analysis methods confirmed the structure of the above polymer.

What is claimed is:

1. A biocide solution comprising a polymer having at least one branched quaternary ammonium unit of the following formula 1:

TABLE 1

Antimicrobial efficacy of samples A and B compared to samples w/o triamine

|  | Sample A w/o triamine | Sample A | Sample B w/o triamine | Sample B | PBS | Control |
|---|---|---|---|---|---|---|
| E. Coli 100 ppm | 0.064/0.090 | 0.071/0.065 | 0.776/0.693 | 0.081/0.079 | 1.781 | 0.037 |
| 10 ppm | 0.203/0.146 | 0.067/0.062 | 0.946/0.842 | 0.561/0.078 | 1.115 | 0.067 |
| 1 ppm | 0.115/0.121 | 0.102/0.059 | 0.849/0.866 | 0.085/0.079 | 1.121 | 0.949 |
| S. Aureus 100 ppm | 0.132/0.107 | 0.083/0.071 | 0.087/0.091 | 0.087/0.094 | 0.481 | 0.037 |
| 10 ppm | 0.204/0.107 | 0.071/0.071 | 0.088/0.088 | 0.078/0.080 | 0.63 | 0.037 |
| 1 ppm | 0.037/0.146 | 0.103/0.093 | 0.094/0.093 | 0.085/0.085 | 1.571 | 0.036 | wherein R1, R2, R3, R4, R5, and R6 independently represent alkyl groups having 1-3 carbon atoms optionally substituted with OH, OMe, OEt, OPr, aryl groups or quaternary ammoniums groups;

linkers represent independently the same or different linkage groups with 2, 3, or more points of connections for quaternary ammonium groups and at least one of the linkers has 3 or more connections or at least 0.01% of the linkers has 3 or more connections; and l, m, and n represent an integer varying from 1 to 5000.

2. A biocide solution of claim 1 wherein: the polymer comprises a branched quaternary ammonium units of the following formula 2 or formula 3:

wherein A, B, C, and D are independently selected from the groups consisting of —$C_2H_4$—, —$C_3H_6$—, —$C_4H_6$—, —$CH_2$—CH(OH)—$CH_2$—, —$CH_2$—CH(OH)—CH(OH)—$CH_2$—, —$CH_2$—CH2-O—CH2-CH2-, —$CH_2$—($C_6H_4$)—$CH_2$—, —$CH_2$—($C_5H_3N$)—$CH_2$—;

R1, R2, R3, R4, R5, R6, R11, R22, R33 and R44 independently represent alkyl groups having 1-3 carbon atoms optionally substituted with —OH, OMe, OEt, OPr, aryl, heteroaryl groups or quaternary ammonium;

R1 and R3 or R2 and R4 or R11 and R33 or R22 and R44 can connect together to form an ethylene or propylene linkage;

L3 represents linkage group with 3, or more points of connections for quaternary ammonium groups;

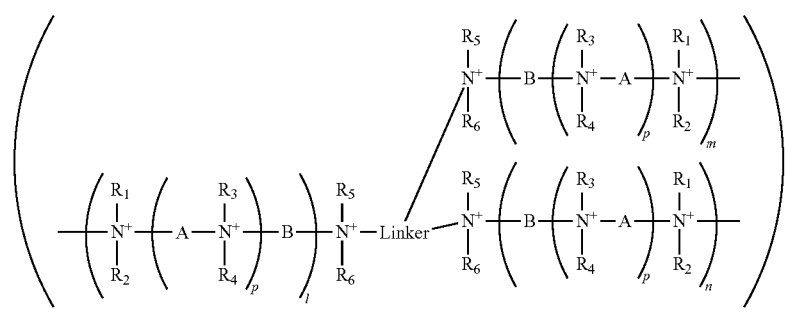

Formula 2

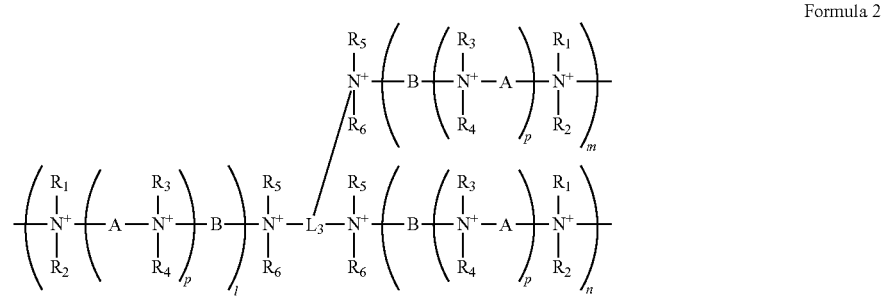

Formula 2

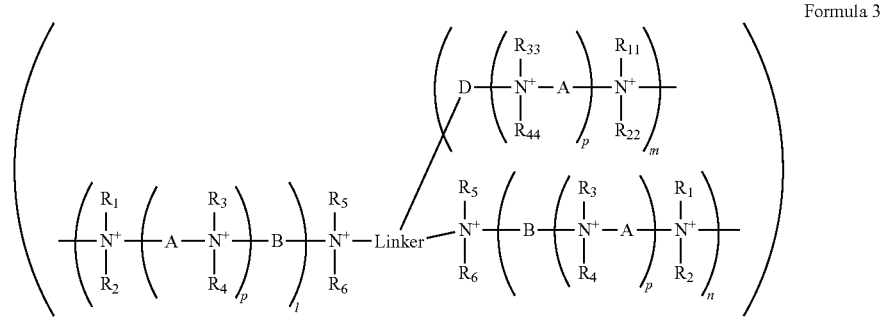

Formula 3

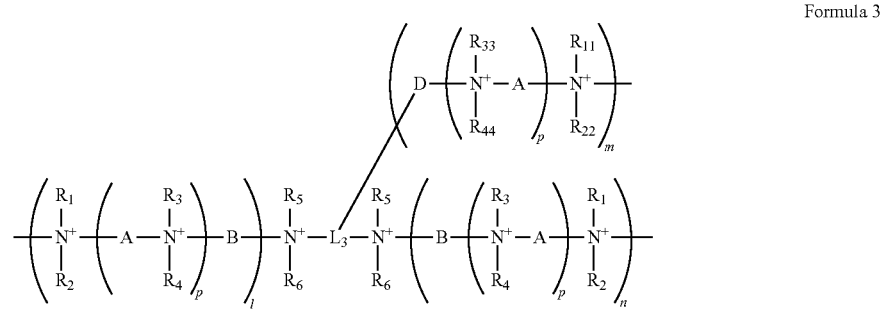

Formula 3

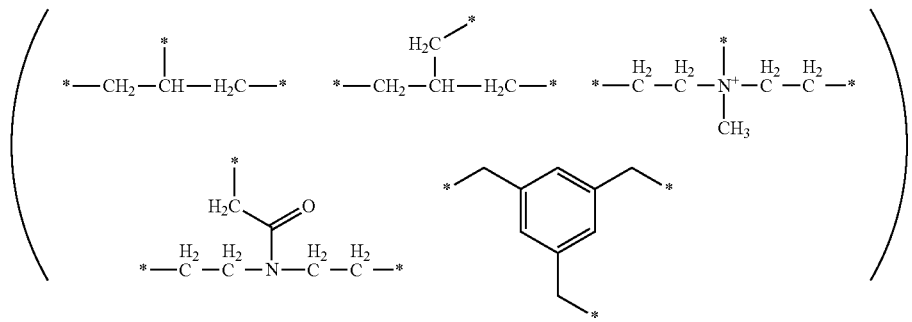

p represents an integer 0 or 1;
l, m, and n independently represent an integer varying from 1 to 1000; and
the counter ions are selected from the group consisting of $F^-$, $Cl^-$, $Br^-$, $SO_4^{-2}$, $HSO^{4-}$, $HCO^{3-}$ and $H_2BO^{3-}$.

3. A biocide solution of claim 2 wherein: the groups represented by A, B, C, and D include —$CH_2$—$CH_2$—, —$CH_2$—$CH_2$—$CH_2$—, —$CH_2$—CH=CH—$CH_2$—, —$CH_2$—CH(OH)—$CH_2$—, —$CH_2$—CH(OH)—CH(OH)—$CH_2$—, —$CH_2$—$CH_2$—O—$CH_2$—$CH_2$—, —$CH_2$—($C_6H_4$)—$CH_2$—, —$CH_2$—($C_5H_3N$)—$CH_2$—;
the groups represented by R1, R2, R3, R4, R5, R6, R11, R22, R33, and R44 include —$CH_3$, —$C_2H_5$, —$C_3H_7$, —$C_3H_6OH$, —$C_3H_6OCH_3$, —$CH_2$—($C_6H_5$), —$CH_2$—($C_6H_4N$), —$CH_2$—($C_6H_4$)—$CH_3$, and $CH_3CH_2$—$N^+$($CH_3$)$_3$, —CH2-, —C2H4- (for ethylene and propylene linkage in claim 2);
L3 represents linkage group with 3, or more points of connections for quaternary ammonium groups, the linkage group consisting one of the following structures;

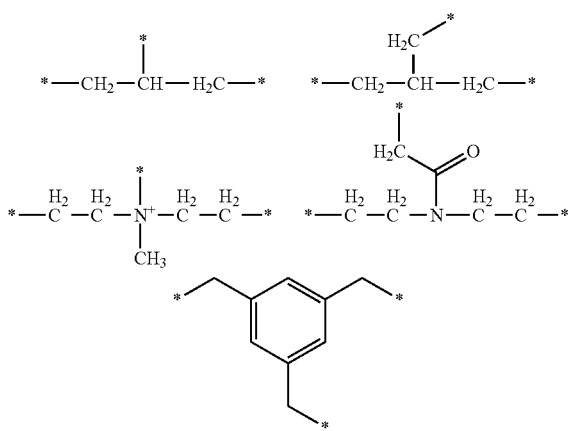

* represents point of connections for quaternary ammonium groups; and
the counter ions is $Cl^-$.

4. A pharmaceutical composition comprising a preservation-effective amount of a polymer according to claim 1.

5. A pharmaceutical composition comprising a preservation-effective amount of a polymer according to claim 2.

6. A pharmaceutical composition comprising a preservation-effective amount of a polymer according to claim 3.

7. A lens care composition comprising a disinfecting-effective amount of a polymer according to claim 1.

8. A lens care composition comprising a disinfecting-effective amount of a polymer according to claim 2.

9. A lens care composition comprising a disinfecting-effective amount of a polymer according to claim 3.

10. An ophthalmic solution comprising a polymer of claim 3, wherein the polymer has a molecular weight between 500 to 200000 to ensure that it is not adsorbed onto and/or absorbed into hydrophilic contact lenses.

11. An ophthalmic solution comprising a polymer of claim 3, wherein the polymer has a molecular weight ranging from 1000 to 100,000.

12. A biocide composition comprising a polymer of claim 3, wherein the composition further includes one or more additional antimicrobial agent, selected from a group consisting of polyhexamethylene biguanide polymers ("PHMB"), polyquarternium-1, myristamidopropyl dimethylamine (Aldox), and amino biguanides.

13. An ophthalmic solution of claim 10, wherein the concentration of the polymer ranges from 0.00005 to 0.05 w/v %.

14. An ophthalmic solution of claim 10, further including an additive selected from the group consisting of viscoelastic agents, chelating agents, and nonionic surfactants.

15. An ophthalmic solution of claim 10, further including an additive selected from the group consisting of dipotassium glycyrrhizinate, sodium edetate, hydroxyethyl cellulose, hydroxypropylmethyl cellulose, polyvinylpyrrolidone, and poloxamer.

16. A biocide composition comprising a polymer of claim 3, further including one or more additional antimicrobial agent, selected from a group consisting of myristamidopropyl dimethylamine, 2-amino-2-methyl-1-propanol, and borate/polyol.

17. A biocide solution of claim 1, wherein ratio of linkers with 3 or more points of connections to linkers with two points of connections is from 0.01% to 50%.

18. A biocide solution of claim 2, wherein ratio of linkers L3 with 3 or more points of connections to linkers with two points of connections is from 0.01% to 50%.

19. A biocide solution of claim 3, wherein ratio of linkers L3 with 3 or more points of connections to linkers with two points of connections is from 0.01% to 50%.

* * * * *